US008739554B2

(12) United States Patent
Federer

(10) Patent No.: US 8,739,554 B2

(45) Date of Patent: Jun. 3, 2014

(54) THERMAL BLOCK UNIT

(75) Inventor: Paul Federer, Wolhusen (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 741 days.

(21) Appl. No.: 12/268,360

(22) Filed: Nov. 10, 2008

(65) Prior Publication Data

US 2009/0120104 A1 May 14, 2009

(30) Foreign Application Priority Data

Nov. 13, 2007 (EP) .................................... 07021983

(51) Int. Cl.

| | |
|---|---|
| ***F25B 21/02*** | (2006.01) |
| ***H01L 37/00*** | (2006.01) |
| ***C03C 25/68*** | (2006.01) |
| ***C12Q 1/68*** | (2006.01) |

(52) U.S. Cl.

USPC .................. 62/3.2; 136/201; 216/94; 435/6.1

(58) Field of Classification Search

USPC .................. 62/3.1, 3.2, 3.3, 3.4, 3.5, 3.6, 3.7; 425/283.1, 286.1, 287.7

See application file for complete search history.

(56) References Cited

U.S. PATENT DOCUMENTS

| | | | | |
|---|---|---|---|---|
| 5,601,141 | A | 2/1997 | Gordon et al. | |
| 5,605,662 | A * | 2/1997 | Heller et al. | 422/68.1 |
| 5,800,989 | A * | 9/1998 | Linn et al. | 435/6.11 |
| 5,849,208 | A * | 12/1998 | Hayes et al. | 216/94 |
| 6,210,882 | B1 * | 4/2001 | Landers et al. | 435/6.12 |
| 6,303,288 | B1 * | 10/2001 | Furcht et al. | 435/4 |
| 7,148,043 | B2 * | 12/2006 | Kordunsky et al. | 435/91.2 |
| 2002/0109844 | A1 * | 8/2002 | Christel et al. | 356/417 |
| 2003/0098984 | A1 * | 5/2003 | Botten et al. | 358/1.4 |
| 2004/0056184 | A1 * | 3/2004 | Steinlechner et al. | 250/231.14 |
| 2005/0145273 | A1 * | 7/2005 | Atwood et al. | 136/201 |
| 2006/0065652 | A1 | 3/2006 | Brown | |
| 2009/0120104 | A1 * | 5/2009 | Federer | 62/3.2 |

FOREIGN PATENT DOCUMENTS

| | | | |
|---|---|---|---|
| EP | 07021983.7 | | 4/2008 |
| WO | 9843740 | A2 | 10/1998 |
| WO | 9843740 | A3 | 10/1998 |
| WO | 9948608 | A2 | 9/1999 |
| WO | 9948608 | A3 | 9/1999 |
| WO | 03022439 | A2 | 3/2003 |
| WO | 03022439 | A3 | 3/2003 |
| WO | 03075111 | A1 | 9/2003 |
| WO | 2004105947 | A2 | 12/2004 |
| WO | 2004105947 | A3 | 12/2004 |
| WO | 2005058501 | A1 | 6/2005 |

* cited by examiner

*Primary Examiner* — Alexandra Elve
*Assistant Examiner* — Henry Crenshaw
(74) *Attorney, Agent, or Firm* — M. Reza Savari

(57) ABSTRACT

The present invention discloses a thermal block unit for thermal treatment of samples comprising temperature regulating units, temperature sensors for measuring temperature at different locations of the thermal block unit, a converter for converting signals from the temperature sensors into digital signals and a thermal block interface for communicating with an instrument.

23 Claims, 2 Drawing Sheets

THERMAL BLOCK UNIT

CROSS-REFERENCES TO RELATED APPLICATIONS

The present application claims the benefit of EP Appl. No. 07021983.7 filed Nov. 13, 2007, the entire content of which is hereby incorporated herein by reference in entirety.

FIELD OF THE INVENTION

The present application relates to the field of devices for thermal treatment of samples in a controlled manner, a system comprising a thermal block unit for thermal treatment of samples and a method for controlled thermal treatment of samples.

BACKGROUND OF THE INVENTION

Devices for the thermal treatment of samples or reaction mixtures in a controlled way are used in several fields of chemistry and biochemistry. For example, it is known that chemical reaction rates are proportional to temperature. Also, the working time or shelf life of a biological samples or laboratory reagents can be increased by keeping the substance at an optimal temperature. Since labor time as well as reagents are expensive) it is desirable to increase the throughput of production and analysis, while at the same time, to minimize the necessary reaction volumes. In general such devices or instruments have a thermal block made of e.g. metal, composite, ceramic or the like, that is in thermal contact with the sample under investigation so that the temperature of the sample is affected by the temperature of the thermal block.

Particularly, a strong need for systems capable of cycling a sample through a range of temperatures, i.e. thermal cyclers, became apparent with the advent of the Polymerase Chain Reaction (PCR), a technique which revolutionized the field of health care and molecular diagnostics.

PCR enables isolation of genomic material, sequencing and the detection of genetic diseases, recombinant DNA techniques, genetic fingerprinting and paternity testing. Viral DNA can likewise be detected by PCR and the amount of virus ("viral load") in a patient can be quantified by PCR-based DNA quantitation techniques or quantitative PCR.

Because the amount of product produced by PCR roughly correlates to the amount of starting material, PCR can be used to estimate the amount of a given sequence that is present in a sample and because of the high sensitivity, virus detection may be possible soon after infection and even before the onset of disease symptoms, thus giving a significant lead in treatment. Quantitative PCR is also useful for determining gene expression levels. In cells, each gene is expressed through the production of messenger RNA (mRNA), which is then used to create a protein corresponding to the gene. The amount of mRNA in the cell for a given gene reflects how active that gene is. By using reverse transcription to produce DNA complementary to the mRNA (called cDNA) and subsequently using PCR to amplify these molecules, the amount of DNA produced for each gives a rough measure of the underlying expression for that gene.

Real-time PCR is a special form of quantitative PCR. By this technique it is possible to simultaneously amplify and quantify a specific part of a given DNA molecule. The DNA is quantified after or during each round of amplification. Two common methods of quantification are the use of fluorescent dyes that intercalate with double-strand DNA, and modified DNA oligonucleotide probes that generate fluorescence at a certain point during the cycle.

PCR specificity and yield as well as throughput are directly related to the ability of the thermal-cycling system to rapidly and accurately arrive at and maintain reaction temperatures for an array of samples in parallel, e.g. in a multiwell plate in contact with a metal thermal block. Heating and cooling is normally achieved by means of temperature regulating units such as thermoelectric coolers (TECs) also called Peltier elements as well as a heat sink. One problem in the prior art is that differences in sample temperature may be generated by non-uniformity of temperature from place to place within the sample block. Temperature gradients may exist within the material of the block, causing some samples to have different temperatures than others at particular times in the cycle. Further, since there are delays in transferring heat from the sample block to the sample, those delays may differ across the sample block. These differences in temperature and delays in heat transfer, commonly referred to as well-to-well inhomogeneity, may cause the yield of the PCR process to differ from sample vial to sample vial. To perform the PCR process successfully and efficiently, and to enable quantitative PCR, these time delays and temperature errors must be minimized to the greatest extent possible.

One state of the art instrument currently available on the market, is the LightCycler® 480 Real-Time PCR System from Roche Diagnostics. This instrument reduces the problem above thanks to a special architecture of the thermal block unit, which comprises also a so-called Therma-Base™ unit, located beneath the Peltier elements, for improved heat transfer and distribution to all samples within a multiwell plate. The heat sink below the Therma-Base® unit features a maximized inner surface area to facilitate rapid heat absorption.

In U.S. Pat. No. 7,133,726B1, it is proposed instead to use a perimeter trench for the heat sink and a perimeter heater around the metal thermal block to reduce edge losses as well as a pin at the center of the assembly establishing a thermal path from the sample block to the heat sink in order to compensate for thermal gradients.

A problem in the state of the art is however represented by the inefficient control of the thermal block unit. Data measured within the thermal block unit, e.g. temperature values, are sent to a controller unit of an instrument and the instrument controls the thermal block unit. An instrument or thermal block test is typically carried out only when the instrument is turned on. One disadvantage is that only a limited number of data are processed, thus making it difficult to react promptly to errors and/or failures and/or any deviation from the normal or expected functioning of the temperature regulating units. Also, data transfer may be unreliable due to the possible influence of the electric connections, e.g. the electric resistance of the cables itself, cracks or line interruptions between thermal block unit and instrument.

SUMMARY OF THE INVENTION

In a first aspect the invention relates to a thermal block unit for thermal treatment of samples comprising a sample block for multiple samples, temperature regulating units, temperature sensors for measuring temperature at different locations of the thermal block unit, a converter for converting signals from the temperature sensors into digital signals, and a thermal block interface for communicating with an instrument.

In a second aspect, the invention relates to a system for thermal treatment of samples comprising an instrument, and the thermal block unit of the invention.

In a third aspect, the invention relates to a method for thermal treatment of samples comprising the steps of providing a thermal block unit according to the invention, measuring the temperature at different locations of the thermal block unit with temperature sensors, converting measured temperature signals into digital signals within the thermal block unit, processing digital signals, and controlling temperature regulating units in response to the processed signals.

BRIEF DESCRIPTION OF THE FIGURES

The invention is explained in more detail below with the aid of the attached drawings. The figures represent the following.

DETAILED DESCRIPTION OF THE INVENTION

Figure 1:
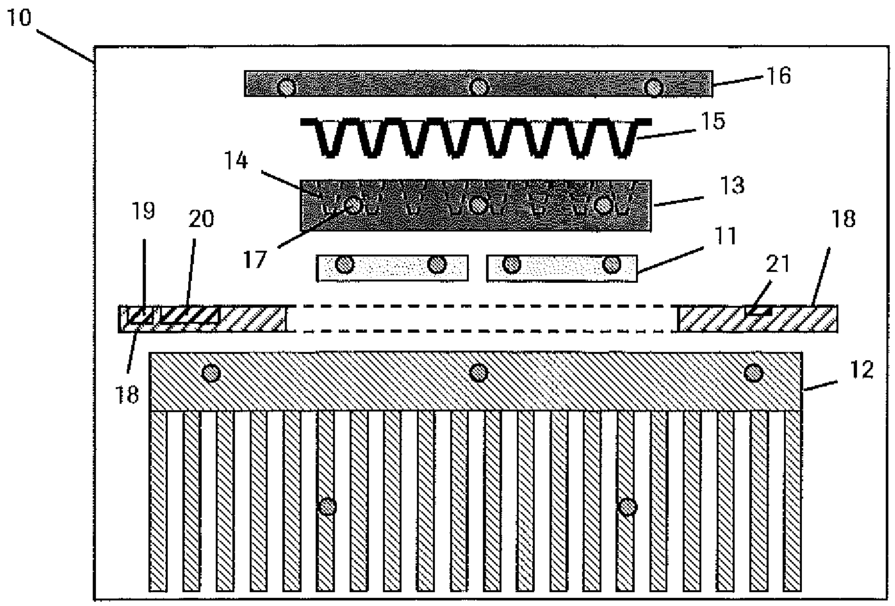
FIG. 1 schematically represents an exploded view of the main components of a thermal block unit.

It is an object of the present invention to provide a thermal block unit for an instrument, the thermal block having improved well-to-well homogeneity and reproducibility.

This is achieved by a more efficient and precise control of the thermal block unit, by converting measured analog parameters into digital signals directly within the thermal block unit. In this way more parameters, i.e. not only temperature but e.g. also current and/or resistances and/or electric potential differences between different parts of the thermal block unit may be measured and more data collected. Digitalization of measured data allows also the use of an increased number of sensors. In this way, even small inhomogeneities can be promptly detected and the temperature regulating units can be controlled accordingly to restore the condition of homogeneity and guarantee reproducibility.

The present invention has the further advantage of avoiding possible data corruption, signal noise, signal instabilities, signal offset and the like, during the communication between the thermal block unit and the instrument. This is possible because digital signals rather than analog signals are transferred from the thermal block unit to the instrument.

A further advantage of the present invention is the reduction of the electronic complexity of the instrument since digital data transmission enables multiplexing. Indeed, several electric components, e.g. cables carrying analog signals, become redundant.

The present invention discloses a thermal block unit for thermal treatment of samples comprising temperature regulating units, temperature sensors for measuring temperature at different locations of the thermal block unit, a converter for converting signals from the temperature sensors into digital signals, and a thermal block interface for communicating with an instrument.

According to the present invention thermal treatment of samples concerns processes by which relatively small volumes, for example less than 1 mL, of chemical or biological samples are exposed to constant temperatures or temperature profiles. This includes for example freezing, thawing, melting of samples; keeping samples at an optimal temperature for a chemical or biological reaction or an assay to occur; subjecting samples to a temperature gradient, e.g. for detecting a characteristic of a sample like the melting point, or the presence of a certain DNA sequence; or subjecting samples to different temperatures varying with time, such as temperature profiles, including temperature cycles, for example, during PCR.

The desired temperature or temperatures are reached and/or maintained by means of temperature regulating units. Temperature regulating units comprise means to provide samples with heat and/or to take up heat from samples in a controlled manner. These means may be fluid-based flow-through systems transporting heat and/or removing heat from the thermal block. These may be also systems utilizing a resistive heating in combination with a dissipative cooling. A summary about thermal management in the field of medical and laboratory equipment is written by Robert Smythe (Medical Device & Diagnostic Industry Magazine, January 1998, p. 151-157), which document is incorporated herein by reference in its entirety In certain embodiments, the temperature regulating units comprise one or more thermoelectric coolers (TECs), also called Peltier elements. TECs are active solid-state heat pumps consisting of a series of p-type and n-type semiconductor pairs or junctions sandwiched between ceramic plates. Heat is absorbed by electrons at the cold junction as they pass from a low energy level in a p-type element to a higher energy level in an n-type element. At the hot junction, energy is expelled to one or more heat sinks as the electrons move from the high-energy n-type element to a low-energy p-type element. A DC power supply provides the energy to move the electrons through the system. The amount of heat pumped is proportional to the amount of current flowing through the TEC; therefore, precise temperature control (<0.01° C.) is possible. Depending on the current direction, TECs can function as coolers as well as heaters. Because of the relatively large amount of heat being pumped over a small area, TECs require a heat sink to dissipate the heat into the ambient environment. The heat sink may be for example made from aluminum because of that metal's relatively high thermal conductivity and low cost and the shape is so designed to maximize the surface area. In this way, the dissipation of heat by surrounding cooler air, especially when using fans (forced convection) is facilitated.

The temperature regulating units may also comprise a ThermaBase™ as incorporated in the LightCycler® System. A ThermaBase™ is a vapor chamber device for transporting and distributing heat. This is a special heat pipe with a substantially planar shape. The term heat pipe is an established name for a sealed vacuum vessel with an inner wick structure that transfers heat by the evaporation and condensation of an internal working fluid. As heat is absorbed at one side of the heat pipe, the working fluid is vaporized, creating a pressure gradient within said heat pipe. The vapor is forced to flow to the cooler end of the heat pipe, where it condenses and dissipates its latent heat to the ambient environment. The condensed working fluid returns to the evaporator via gravity or capillary action within the inner wick structure. A ThermaBase™ in general is a passive device, but it can be designed as an active device, too, if it is equipped with control means. Such control means may, for example modify the thermal conductivity of the thermal base by adjusting either the flow rate within the enclosure or the volume of the enclosure affecting the vacuum within the vessel.

According to the present invention temperature sensors are sensors providing a measurable analog signal which is related to temperature. In a certain embodiment, this signal is an electrical signal. Temperature sensors can be transducers that exploit the predictable change in electrical resistance of some materials with changing temperature. These may be for example chosen from the group of temperature sensitive resistors, e.g. thermistors or resistance temperature detectors. Thermistors can be of two types. If the resistance increases with increasing temperature, they are called positive temperature coefficient (PTC) thermistors. If the resistance decreases with increasing temperature, they are called negative temperature coefficient (NTC) thermistors. Thermistors differ from resistance temperature detectors (RTDs) in that the material used in a thermistor is generally a ceramic or polymer, while RTDs use pure metals, usually platinum. The temperature response is also different.

In an embodiment, electric potential differences and/or currents and/or resistances within the thermal block unit, for example between different locations of the temperature regulating units, e.g. between different Peltier elements, are further measured and converted into digital signals. Electric circuits or components, like resistors, switches, bridges, operational amplifiers, and the like, for carrying out such measurements may be therefore also integrated within the thermal block unit.

The term "within" in the present description is used with the general meaning of "comprised", "at some location, which is part of", "physically attached or bound to". It may refer to something on the surface, into a recess, or enclosed in the body.

A thermal block interface according to the present invention is part of an electronic system comprised within the thermal block unit by which electronic communication between the thermal block unit and an instrument can be established. The thermal block interface may be for example in the form of a printed circuit board (PCB). In the state of the art of thermal blocks, the interface consists of analog lines and sockets or plugs to guide currents or analog signals from the thermal block unit to the instrument and vice versa, wherein the instrument controls certain properties or actions of the thermal block unit. According to the present invention the thermal block interface is capable of sending digital signals to an instrument thanks to a converter converting analog signals from the temperature sensors and/or other measured parameters like electric potential differences, currents, resistances, and the like into digital signals.

Digital signals are digital representations of discrete-time signals derived from analog signals. Analog signals refer to data which may change over time, e.g. the temperature at a given location of the thermal block unit, or the potential difference at some node in a circuit, which can be represented as a mathematical function, i.e. signal as a function of time. A discrete-time signal is a sampled analog signal, i.e. the data value is noted at fixed intervals rather than continuously. If individual time values of the discrete-time signal, instead of being measured precisely (which would require an infinite number of digits), are approximated to a certain precision, which, therefore, only requires a specific number of digits, then the resultant data stream is termed a digital signal. The process of approximating the precise value within a fixed number of digits, or bits, is called quantization. Digital signals can be therefore represented as binary numbers.

A converter according to the present invention is therefore for example a converter for converting measured analog data into digital signals. Suitable analog-to-digital converters (ADC) are known in the art.

One advantage of digital data is the option of multiplexing. Several analog signals can be processed by one analog-to-digital converter (ADC), and resulting digital signals can be transferred using one or a few wires. This means also low electronic requirements in terms of cables, sockets, and/or power. Another advantage is the increased data transfer safety of digital data, by including e.g. redundancy checks, like checksums, and the like.

The thermal block unit may further comprise a thermal block processor for processing digital signals directly within the thermal block unit. The thermal block processor may comprise the ADC or the ADC may be separated from it.

Processing comprises monitoring the correct functioning of the thermal block unit via the converted measured data and controlling the thermal block unit by reacting promptly to errors and/or failures and/or for example to the minimum bias from homogeneity. This is e.g. done by adjusting the current flow to individual temperature regulating units to restore the condition of homogeneity and guarantee reproducibility.

Samples are often provided within standard multiwell plates, e.g. in the 96- or 384-well format, or tubes. The thermal block unit may therefore further comprise a sample block, The sample block is a holder for multiple sample vials in a manner that heat exchange can be facilitated. The sample block may be for example a multi-well-plate holder or a tube holder and may be made of a material with low thermal mass for rapid temperature changes, for example metal, such as aluminum or silver. The sample block is in close thermal contact with the temperature regulating units.

The thermal block unit may for example comprise further a heatable cover to prevent condensation of liquid vapor which may take place within the sample well or tube during heating. This cover is so designed to match from the top the shape of the multi-well-plate or the tubes used. In an embodiment, it exercises also pressure to keep the samples closed during thermal treatment and maximize thermal contact. The cover may also feature holes for optical detection of samples.

The thermal block unit may further comprise a memory, e.g. an EEPROM or flash memory, for storing block specific data, such as for example a serial number, the block type, and/or calibration parameters. The memory may further store data which are generated during use of the thermal block) e.g. dates, errors, and/or thermal block specific counts, e.g. how many temperature cycles were carried out.

In certain embodiments, the thermal block unit may be a thermal block cycler, which means a thermal block unit capable of cycling samples through a range of temperatures or temperature profile, e.g. as required for PCR.

The present invention refers also to a system for thermal treatment of samples comprising an instrument, and a thermal block unit, the thermal block unit comprising temperature regulating units, temperature sensors for measuring temperature at different locations of the thermal block unit, a converter for converting signals from the temperature sensors into digital signals, and a thermal block interface for communicating with the instrument.

An instrument according to the present invention may be an apparatus for assisting users with the thermal treatment of samples, i.e. by facilitating the operation and use of the thermal block unit interfaced to the instrument.

In a certain embodiment, the thermal block unit may be releasably held within the instrument. In this way different thermal block units, e.g. carrying different sample blocks and covers may be used, exchanged, and/or replaced, depending on the application or in case of damage without limiting the use of the instrument.

The instrument may conveniently comprise a detection unit, e.g. an optical detection unit, for detecting the result or the effect of the thermal treatment of samples. The optical detection unit may comprise a light source, e.g. a xenon lamp, the optics, e.g. mirrors, lenses, optical filters, and/or fiber optics, for guiding and filtering the light, one or more reference channels, and a CCD camera.

The instrument may conveniently comprise a loading unit for loading/unloading micro-well plates or tube arrays. The loading unit may comprise a drawer and retainer for multiwell plates, DC-motors for movement of the plates and opening/closing/pressing the heatable cover, sensors to identify the type of plate, and/or a barcode reader, e.g. to identify samples.

According to some embodiments the interface may send converted digital signals to the instrument.

The instrument may further comprise a controller processor for processing the digital signals received from the thermal block unit via the thermal block interface. The controller processor may have also or in the alternative other functions as well) like for example controlling the loading unit.

The instrument may further comprise a system processor for the control of the system, i.e. a processor running a real-time operating system (RTOS), which is a multitasking operating system intended for real-time applications. In other words the system processor may be capable of managing real-time constraints, i.e. operational deadlines from event to system response regardless of system load. It controls in real time that different units within the system operate and respond correctly according to given instructions.

The instrument may further comprise most of the other electronic components, like pulse-width-modulators and H-Bridges that may be needed for controlling the temperature regulating units in response to the processed digital signals. Such electronic components may however also be comprised or in the alternative within the thermal block unit, e.g. within the thermal block interface.

The present invention refers also to a method for thermal treatment of samples comprising the steps of measuring the temperature at different locations in the thermal block unit with temperature sensors, converting measured temperature signals into digital signals within the thermal block unit, processing digital signals, and controlling temperature regulating units in response to the processed signals.

The method may further comprise the step of measuring electric potential differences and/or currents and/or resistances within the thermal block unit and converting the measured signals into digital signals.

According to one embodiment, the method may further comprise the step of processing the digital signals by a thermal block processor integrated with the thermal block unit, directly within the thermal block unit, wherein processing comprises monitoring the correct functioning of the thermal block unit via the converted measured data and reacting promptly to errors and/or for example to the minimum bias from homogeneity.

The method may further comprise the step of sending digital signals to an instrument via a thermal block interface and processing the digital signals by a controller processor within the instrument.

According to one embodiment converted digital signals are sent directly to the controller processor.

According to another embodiment, both a controller processor within the instrument and a thermal block processor within the thermal block unit contribute to process the digital signals by communicating between them, sharing part of the operations or delegating part of the operations to the other.

The method may further comprise the step of exposing one or more samples to a temperature profile, wherein the temperature profile may comprise repeated temperature cycles, e.g. as required for PCR.

In FIG. 1 a thermal block unit 10 according to one embodiment is shown. The thermal block unit 10 comprises temperature regulating units such as one or more Peltier elements 11 and one or more heat sinks 12. The Peltier elements 11 may be in direct thermal contact with the heat sink 12. However, a ThermaBase™ heat sink, (not shown) may be located between Peltier elements 11 and heat sinks 12. Moreover a sample block 13 may be in close thermal contact with the Peltier elements 11 from the other side. Sample block 13 may be made of for example metal such as e.g. aluminum or silver and comprise recesses 14 for receiving e.g. a multiwell plate 15. A heatable cover 16 may be pressed on top of the multiwell plate 15 in order to keep the samples closed during thermal processing and to prevent condensation of sample vapors within the wells or tubes. The heatable cover 16 may comprise holes, e.g. in correspondence of each sample, for optical detection. Temperature sensors 17 measure the temperature at different locations of the thermal block unit 10, e.g. at different locations of the Peltier elements 11, of the heat sink 12, of the sample block 13, and/or of the heatable cover 16. In a certain embodiment, electric potential differences and/or currents and/or resistances within the thermal block unit 10, for example between different locations of the temperature regulating units, e.g. of the Peltier elements 11, are further measured. Electric circuits or components, like resistors, switches, bridges, and the like for carrying out such measurements may be therefore also integrated (not shown) within the thermal block unit 10.

The thermal block unit 10, may comprise a thermal block interface 18, by which electronic communication between the thermal block unit 10 and an instrument 30 can be established. The thermal block interface 18 may be in the form of a printed circuit board (PCB) comprising most of the electronic circuits or components within the thermal block unit 10. The thermal block interface 18, can comprise a converter 19 converting analog signals from the temperature sensors and/or other measured parameters like electric potential differences, currents, and/or resistances, into digital signals.

The thermal block interface 18, may further comprise a thermal block processor 20 for processing digital signals directly within the thermal block unit 10. The thermal block processor 20 may comprise the converter 19 or may be separated from it.

The thermal block interface 18, may further comprise a memory 21, e.g. an EEPROM or flash memory, for storing block specific data like for example a serial number, the block type, calibration parameters and/or data which are generated during use of the thermal block unit 10.

Figure 2:
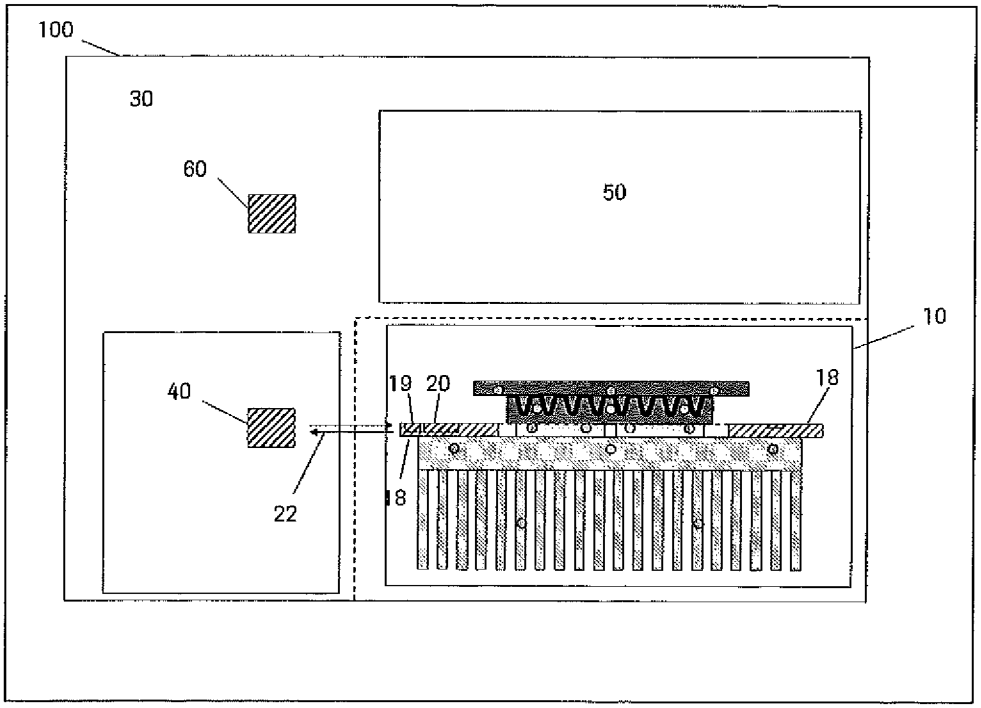
FIG. 2 schematically represents a system for thermal treatment of samples comprising an instrument and a thermal block unit.

FIG. 2 represents schematically a system 100 for thermal treatment of samples comprising an instrument 30 and a thermal block unit 10. According to a certain embodiment, the thermal block unit 10 is releasably received within the instrument 30. The thermal block unit 10 communicates with the instrument 30 via the thermal block interface 18.

According to another embodiment, the thermal block unit 10 sends digital signals 22 to the instrument 30 via the thermal block interface 18.

The instrument 30 may comprise a controller processor 40 for processing the digital signals 22 received from the thermal block unit 10 via the thermal block interface 18.

According to another embodiment digital signals 22 are sent directly to the controller processor 40 after conversion by the converter 19.

According to another embodiment, both a controller processor 40 within the instrument 30 and a thermal block processor 20 within the thermal block unit 10 contribute to processing digital signals by communicating between them, sharing part of the operations and/or delegating part of the operations to the other.

The instrument 30 may further comprise most of the other electronic components, like pulse-width-modulators and H-Bridges (not shown) that may be needed for controlling the temperature regulating units 11,12 in response to the processed digital signals. Such electronic components may however be comprised also or in alternative within the thermal block unit 10, e.g. within the thermal block interface 18.

The instrument 30 can further comprise an optical detection unit 50, and a loading unit (not shown).

The instrument may further comprise a system processor 60 for the control of the system 100.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations.

What is claimed is:

1. A thermal block unit for thermal treatment of samples comprising:

a plurality of temperature regulating units comprising one or more thermoelectric coolers and a heat sink, a sample block for holding multiple sample vials, the sample block being in close thermal contact with the thermoelectric coolers, wherein the thermoelectric coolers are positioned over the heat sink and between the sample block and the heat sink, and the number of the thermoelectric coolers is less than the number of the sample vials.

a heatable cover for closing the sample vials and preventing condensation of sample vapors within the sample vials, the heatable cover comprising holes in correspondence of each sample in the sample vials for optical detection, one or more temperature sensor(s) for measuring temperature at one or more different locations of the thermal block unit, wherein the number of the temperature sensors is less than the number of sample vials held by the sample block, and the number of temperature regulating units is less than the number of sample vials held by the sample block, one or more converter(s) for converting signals from the temperature sensors into digital signals, at least one processor for processing said digital signals and configured to control the one or more temperature regulating units to restore condition of well-to-well homogeneity and reproducibility in case of a minimum bias from homogeneity, and one or more thermal block interface(s) for communicating with an instrument.

2. The thermal block unit according to claim 1 wherein said at least one processor comprises a thermal block processor for processing said digital signals directly within the thermal block unit.

3. The thermal block unit according to claim 1 wherein the thermal block interface is effective to send said digital signals to the instrument.

4. The thermal block unit according to claim 1 wherein the temperature regulating units comprise Peltier elements and a heat sink.

5. The thermal block unit according to claim 1 further comprising a memory.

6. The thermal block unit of claim 5 wherein the memory stores data selected from the group consisting of: thermal block specific counts, serial number, block type, calibration parameters, dates and errors.

7. The thermal block unit according to claim 1 wherein the thermal block unit is a thermal block cycler.

8. A system for thermal treatment of samples, comprising:

an instrument, and a thermal block unit according to claim 1.

9. The system according to claim 8 wherein the at least one processor of the thermal block unit comprises a thermal block processor for processing said digital signals directly within the thermal block unit.

10. The system according to claim 8 wherein the interface is effective to send said digital signals to the instrument.

11. The system according to claim 8 wherein the instrument comprises a controller processor for processing said digital signals.

12. The system according to claim 8 wherein the thermal block unit is releasably received within the instrument.

13. The system according to claim 8 wherein the instrument further comprises an optical detection unit.

14. The system according to claim 8 wherein the instrument further comprises a loading unit for loading/unloading multiwell plates or tube arrays.

15. The system according to claim 9 wherein the instrument comprises a system processor for the control of the system.

16. A method for thermal treatment of samples comprising:

providing a thermal block unit according to claim 1, measuring the temperature at different locations of the thermal block unit with the temperature sensors, converting measured temperature signals into digital signals within the thermal block unit, processing digital signals, and controlling the temperature regulating units in response to the processed signals.

17. The method of claim 16 wherein processing of digital signals is carried out by a thermal block processor integrated within the thermal block.

18. The method according to claim 16 further comprising sending digital signals to an instrument.

19. The method of claim 18, wherein processing of digital signals is carried out by a controller processor within the instrument.

20. The method according to claim 16 further comprising exposing one or more samples to a temperature profile.

21. The method according to claim 20 wherein the temperature profile comprises repeated temperature cycles.

22. The thermal block unit according to claim 1 wherein the plurality of temperature regulating units control the temperature at <0.01° C. across the thermal block unit.

23. The thermal block unit according to claim 1, further comprising one or more components for measuring and converting into digital signals one or more of electric potential differences, and/or currents, and/or resistances within the thermal block.

* * * * *